(12) United States Patent
Hennard

(10) Patent No.: US 8,882,811 B1
(45) Date of Patent: Nov. 11, 2014

(54) SPINAL IMPLANT SYSTEM AND METHOD

(71) Applicant: Warsaw Orthopedic, Inc., Warsaw, IN (US)

(72) Inventor: Michelle M. Hennard, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 13/923,593

(22) Filed: Jun. 21, 2013

(51) Int. Cl.
*A61B 17/70* (2006.01)
(52) U.S. Cl.
CPC .................................. *A61B 17/7049* (2013.01)
USPC ........................................................ 606/279
(58) Field of Classification Search
USPC .......... 606/279, 246, 264, 265, 99, 104, 86 A
See application file for complete search history.

(56) References Cited

U.S. PATENT DOCUMENTS 7,527,638 B2 * 5/2009 Anderson et al. ............. 606/279

* cited by examiner

*Primary Examiner* — Pedro Philogene
*Assistant Examiner* — David Comstock
(74) *Attorney, Agent, or Firm* — Sorell Lenna & Schmidt LLP

(57) ABSTRACT

A method for treating a spine includes creating a single minimally invasive incision in tissue; manipulating a lateral portion without manipulating a contralateral portion of the tissue to deliver fasteners and a rod through the incision, the fasteners being delivered along cortical trajectories disposed in alignment with vertebral levels; fastening the fasteners with the vertebral levels adjacent the lateral portion; connecting the rod with the fasteners; manipulating the contralateral portion without manipulating the lateral portion to deliver fasteners and a rod through the incision, the fasteners being delivered along cortical trajectories disposed in alignment with the vertebral levels; fastening the fasteners with the vertebral levels adjacent the contralateral portion; and connecting the rod with the fasteners. Systems and implants are disclosed.

20 Claims, 6 Drawing Sheets

SPINAL IMPLANT SYSTEM AND METHOD

TECHNICAL FIELD

The present disclosure generally relates to medical devices for the treatment of musculoskeletal disorders, and more particularly to a surgical system for implant delivery to a surgical site and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, laminectomy and implantable prosthetics. As part of these surgical treatments, spinal constructs, such as, for example, bone fasteners, spinal rods and interbody devices can be used to provide stability to a treated region. For example, during surgical treatment, surgical instruments can be used to deliver components of the spinal constructs to the surgical site for fixation with bone to immobilize a joint. This disclosure describes an improvement over these prior art technologies.

SUMMARY

In one embodiment, a method for treating a spine is provided. The method comprises the steps of: creating a single minimally invasive incision in tissue of a body along a substantially sagittal plane of the body; manipulating a lateral portion of the tissue without manipulating a contralateral portion of the tissue to deliver a first fastener, a second fastener and a first spinal rod through the incision, the first fastener being delivered along a cortical trajectory disposed in alignment with a first vertebral level and the second fastener being delivered along a cortical trajectory disposed in alignment with a second vertebral level; fastening the first fastener with the first vertebral level adjacent the lateral portion; fastening the second fastener with the second vertebral level adjacent the lateral portion; connecting the first spinal rod with the fasteners; manipulating the contralateral portion without manipulating the lateral portion to deliver a third fastener, a fourth fastener and a second spinal rod through the incision, the third fastener being delivered along a cortical trajectory disposed in alignment with the first vertebral level and the fourth fastener being delivered along a cortical trajectory disposed in alignment with the second vertebral level; fastening the third fastener with the first vertebral level adjacent the contralateral portion; fastening the fourth fastener with the second vertebral level adjacent the contralateral portion; and connecting the second spinal rod with the third and fourth fasteners. In some embodiments, implants and systems are disclosed.

BRIEF DESCRIPTION OF THE DRAWINGS

The present disclosure will become more readily apparent from the specific description accompanied by the following drawings, in which.

DETAILED DESCRIPTION

Figure 1:
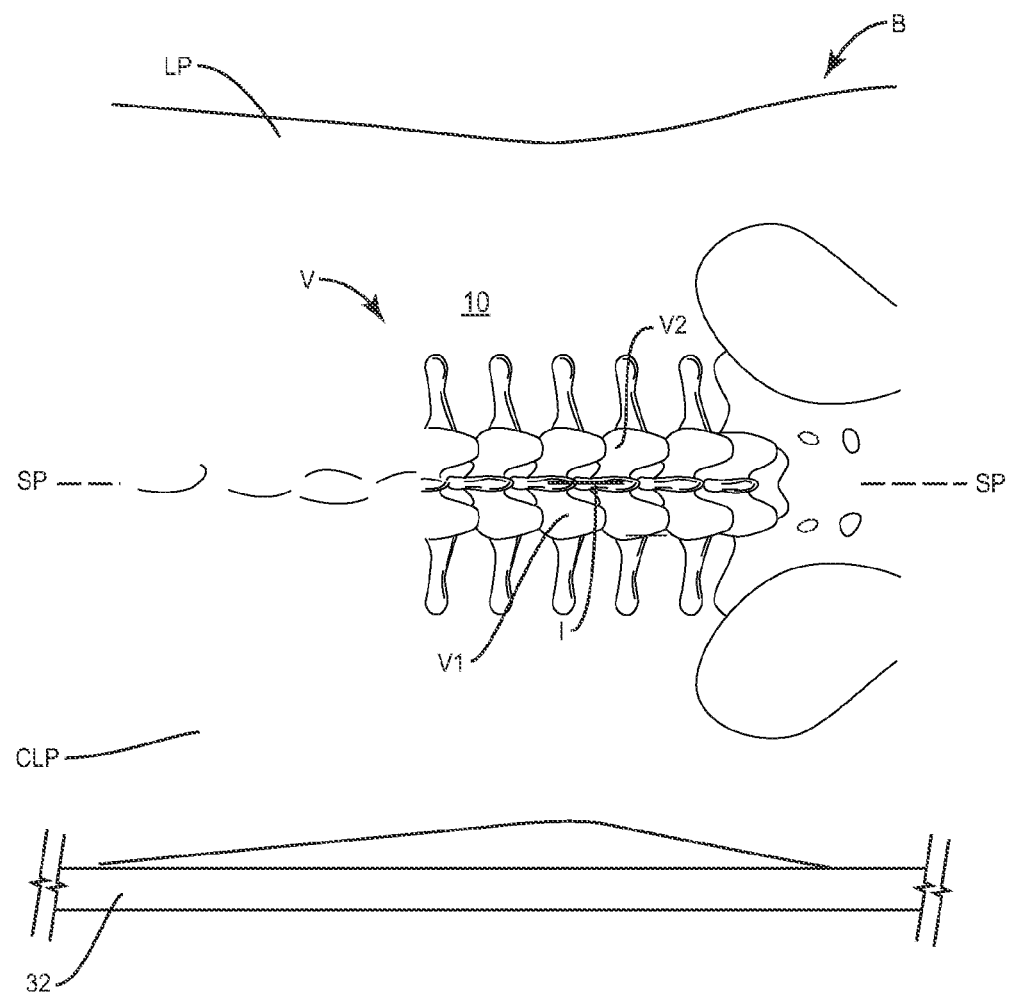
FIG. 1 is a plan view of one embodiment of a system in accordance with the principles of the present disclosure disposed with a body.

The exemplary embodiments of the surgical system and related methods of use disclosed are discussed in terms of medical devices for the treatment of musculoskeletal disorders and more particularly, in terms of a surgical system for implant delivery to a surgical site and a method for treating a spine. In one embodiment, the systems and methods of the present disclosure are employed with a spinal joint and fusion, for example, with a cervical, thoracic, and/or lumbar region of a spine. In one embodiment, the systems and methods can be employed with a spinal fusion, such as, for example, a posterior joint fusion.

In one embodiment, the system is employed with a method for implanting components of a system with a body of a patient when the body is disposed in a lateral position with a surgical fixed surface, such as, for example, a surgical table. In some embodiments, the systems and methods of the present disclosure can be employed with the body disposed in a prone position. In some embodiments, the systems and methods of the present disclosure can be employed with a direct lateral interbody fusion procedure. In one embodiment, the method includes implanting a plate through a lateral incision to support a selected side, such as, for example, a lateral side after inserting an interbody implant and implanting unilateral bone screws to support a contra-lateral side.

In one embodiment, the method includes inserting bone fasteners, such as, for example, bone screws into vertebrae of a patient along a cortical trajectory for bilateral fixation without moving the patient from an initial position, such as, for example, a lateral position. In some embodiments, the cortical trajectory is modified such that an extender disposed with vertebrae does not contact a spinous process of the vertebrae. In one embodiment, the cortical trajectory is 1-2 millimeters (mm) lateral from a starting point to provide space for an extender. In some embodiments, the cortical trajectory allows bone screws to be positioned on a lateral and a contralateral side of the vertebrae when a patient is in the lateral position.

In one embodiment, at least two spinal rods are placed through one minimally invasive incision without creating a second incision on each side of the vertebrae. In one embodiment, the method includes inserting an interbody vertebral spacer between vertebrae without rotating the patient. In one embodiment, bone screws are placed in the lateral and contralateral sides of the vertebrae. In one embodiment, the bone screws on the same vertebral level of vertebrae are substantially parallel.

In some embodiments, the method is used with surgical navigation, such as, for example, fluoroscope or image guidance. In some embodiments, the presently disclosed systems and methods reduce operating time for a surgical procedure and reduce radiation exposure due to fluoroscope or image guidance, for example, by eliminating procedural steps and patient repositioning by implanting system components in one body position.

In one embodiment, the systems and methods of the present disclosure can include making a percutaneous cortical incision, which can include one small centerline incision; pulling back tissue and inserting extenders on a side, such as, for example, a lateral side of a construct to implant bone fasteners; passing a spinal rod through the extenders and fasteners and removing the extenders; and pulling back tissue and inserting extenders on a side, such as, for example, a contra-lateral side of a construct to implant bone fasteners; passing a contra-lateral spinal rod through the extenders and fasteners and removing the extenders.

In one embodiment, one or all of the components of the surgical system are disposable, peel-pack, pre-packed sterile devices. One or all of the components of the surgical system may be reusable. The surgical system may be configured as a kit with multiple sized and configured components.

In one embodiment, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In one embodiment, the present disclosure may be employed with other osteal and bone related applications, including those associated with diagnostics and therapeutics. In some embodiments, the disclosed surgical system and methods may be alternatively employed in a surgical treatment with a patient in a prone position, supine position, lateral position and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to exemplary embodiments of the present disclosure, which are illustrated in the accompanying figures. Turning to FIGS. 1-7, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites, depending on the particular application and/or preference of a medical practitioner. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Figure 6:
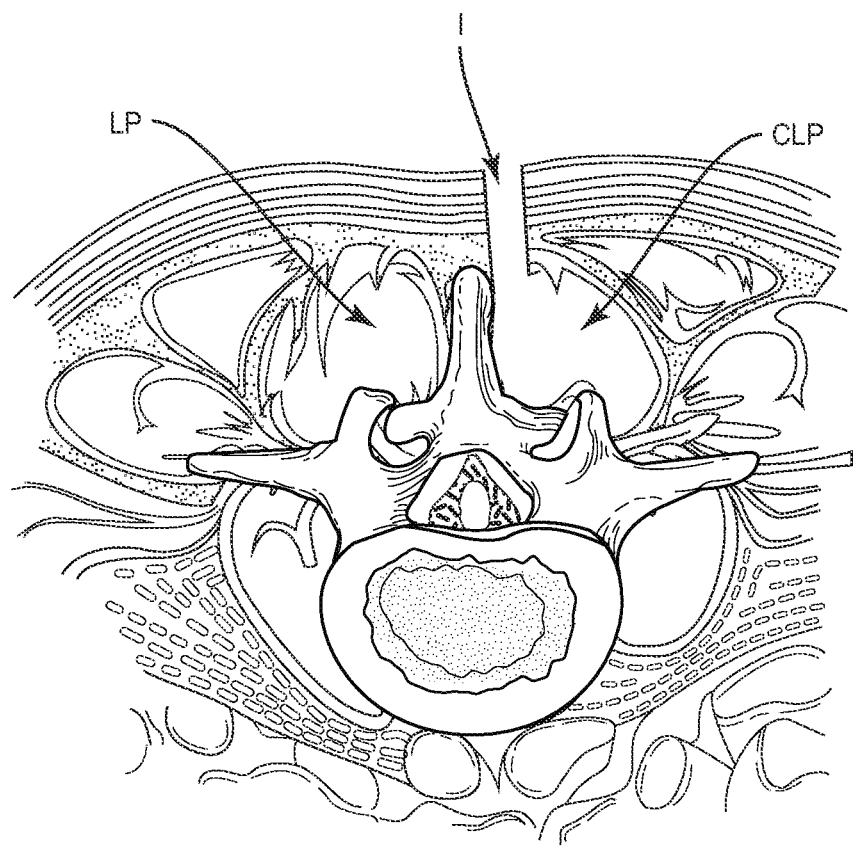
FIG. 6 is a cross section view of components of the system and the body shown in FIG. 1.

Spinal implant system 10 is employed, for example, with a minimally invasive procedure, including percutaneous techniques, and mini-open surgical techniques to deliver and introduce instrumentation and/or an implant, such as, for example, a bone fastener, at a surgical site within a body B of a patient, which includes, for example, a spine having vertebrae V. Spinal implant system 10 includes an extender 12 (FIG. 4) and fasteners 16, 18, 20, 22 (FIG. 6). Extender 12 is configured for inserting a fastener into vertebrae V. In some embodiments, a retractor (not shown) is configured to retract tissue, such as, for example, a lateral portion LP of the tissue and/or a contra-lateral portion CLP of the tissue disposed adjacent a minimally invasive incision I to create an access path to a surgical site including vertebrae V. In some embodiments, system 10 may comprise various instruments, such as, for example, inserters, reducers, spreaders, distractors, blades, clamps, forceps, elevators and drills, which may be alternately sized and dimensioned, and arranged as a kit.

In some embodiments, one or more of fasteners 16, 18, 20, 22 may be engaged with tissue in various orientations, such as, for example, series, parallel, offset, staggered and/or alternate vertebral levels. In some embodiments, one or more of fasteners 16, 18, 20, 22 may comprise multi-axial screws, sagittal angulation screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

Each of fasteners 16, 18, 20, 22 comprise a first portion, such as, for example, a receiver and a second portion, such as, for example, an elongated shaft configured for penetrating tissue. The receiver includes a pair of spaced apart arms having an inner surface that defines a U-shaped passageway. One of more of the passageways are configured for disposal of a longitudinal element, such as, for example, a spinal rod 28 and/or a spinal rod 30. In some embodiments, all or only a portion of the passageway may have alternate cross section configurations, such as, for example, oval, oblong, triangular, square, polygonal, irregular, uniform, non-uniform, offset, staggered, and/or tapered. In some embodiments, the arms of the receiver may be disposed at alternate orientations, relative to the shaft, such as, for example, those alternatives described herein.

In one embodiment, each of fasteners 16, 18, 20, 22 have a multi axial configuration such that the receiver is rotatable to a selected angle through and within an angular range to capture a spinal rod for fixation therein. The inner surface of the receiver includes a thread form configured for engagement with a coupling member, such as, for example, a set screw. The set screw is threaded with the receiver to attach, provisionally fix and/or lock spinal rods 28, 30 with at least one of fasteners 16, 18, 20, 22.

The shaft has a cylindrical cross section configuration and includes an outer surface having an external thread form. In some embodiments, the external thread form may include a single thread turn or a plurality of discrete threads. In some embodiments, other engaging structures may be located on the shaft, such as, for example, a nail configuration, barbs, expanding elements, raised elements and/or spikes to facilitate engagement of the shaft with tissue, such as, for example, vertebrae.

In some embodiments, all or only a portion of the shaft may have alternate cross section configurations, such as, for example, oval, oblong, triangular, square, polygonal, irregular, uniform, non-uniform, offset, staggered, undulating, arcuate, variable and/or tapered. In some embodiments, the outer surface of the shaft may include one or a plurality of openings. In some embodiments, all or only a portion of the outer surface of the shaft may have alternate surface configurations, such as, for example, smooth and/or surface configurations to enhance fixation with tissue, such as, for example, rough, arcuate, undulating, porous, semi-porous, dimpled, polished and/or textured. In some embodiments, all or only a portion of the shaft may be cannulated.

Each of spinal rods 28, 30 have a cylindrical cross section configuration. In some embodiments, system 10 may include one or a plurality of spinal rods, which may be relatively disposed in a side by side, irregular, uniform, non-uniform, offset and/or staggered orientation or arrangement. In some embodiments, spinal rods 28, 30 can have a uniform thickness/diameter. In some embodiments, spinal rods 28, 30 may have various surface configurations, such as, for example, rough, threaded for connection with surgical instruments, arcuate, undulating, dimpled, polished and/or textured. In some embodiments, the thickness defined by spinal rods 28, 30 may be uniformly increasing or decreasing, or have alternate diameter dimensions along its length. In some embodiments, spinal rods 28, 30 may have various cross section configurations, such as, for example, oval, oblong, triangular, rectangular, square, polygonal, irregular, uniform, non-uniform, variable and/or tapered. In some embodiments, spinal rods 28, 30 may have various lengths. In some embodiments, the longitudinal element may include one or a plurality of tethers.

In some embodiments, the longitudinal element may have a flexible configuration and fabricated from materials, such as, for example, polyester, polyethylene, fabric, silicone, polyurethane, silicone-polyurethane copolymers, polymeric rubbers, polyolefin rubbers, elastomers, rubbers, thermoplastic elastomers, thermoset elastomers and elastomeric composites. In one embodiment, the flexibility of the longitudinal element includes movement in a lateral or side to side direction and prevents expanding and/or extension in an axial direction. In some embodiments, all or only a portion of the longitudinal element may have a semi-rigid, rigid or elastic configuration, and/or have elastic properties, such as the elastic properties corresponding to the material examples described above. In some embodiments, the longitudinal element may be compressible in an axial direction.

In assembly, operation and use, spinal implant system 10, similar to the systems described herein, is employed with a surgical procedure for treatment of a spinal disorder, such as those described herein, affecting a section of a spine of a patient. System 10 may also be employed with other surgical procedures. To treat a section of vertebrae V, body B of a patient is disposed in a lateral orientation, as shown in FIG. 1, relative to a surgical fixed surface, such as, for example, surgical table 32 configured for supporting body B. Body B includes lateral portion LP and contra-lateral portion CLP. Portion CLP is disposed between portion LP and surgical table 32 when body B is disposed in the lateral orientation. In some embodiments, the components, such as, implants including bone fasteners, rods, interbody devices and plates, of spinal implant system 10 are delivered and implanted with body B while maintaining body B in the lateral orientation, not rotating body B from the lateral orientation and/or not moving body B into one or a plurality of alternate orientations relative to surgical table 32. This configuration and method of use of spinal implant system 10 reduces operating time for a surgical procedure and reduces radiation exposure due to fluoroscope or image guidance, for example, by eliminating procedural steps and patient repositioning by implanting system components in one body position. In one embodiment, body B is disposed in a prone orientation relative to surgical table 32.

With body B disposed in a selected orientation, a medical practitioner obtains access to a surgical site including a vertebral level V1 and a vertebral level V2 of vertebrae V through a single minimally invasive incision I in tissue, which includes soft tissue and/or muscle, of body B along a sagittal plane SP of body B. In one embodiment, incision I is laterally offset 1-2 mm from sagittal plane SP. In some embodiments, incision I is approximately a two inch incision over a spinous process SPP to the dorsolumbar fascia.

The tissue comprising lateral portion LP includes soft tissue comprising muscle, ligaments, tendons, cartilage and/or bone, which is disposed adjacent incision I. Lateral portion LP of the soft tissue is manipulated to create an opening and access path to a surgical site including vertebrae V of lateral portion LP without selectively manipulating contralateral portion CLP, which includes soft tissue comprising muscle, ligaments, tendons, cartilage and/or bone of the tissue. For example, a dorsolumbar fascia of lateral portion LP is opened exposing an erector spinae aponeurosis. A dissection is made along spinous process SPP over the lamina to elevate the multifidus to provide a lateral window to the lamina and articular process of lateral portion LP.

Figure 2:
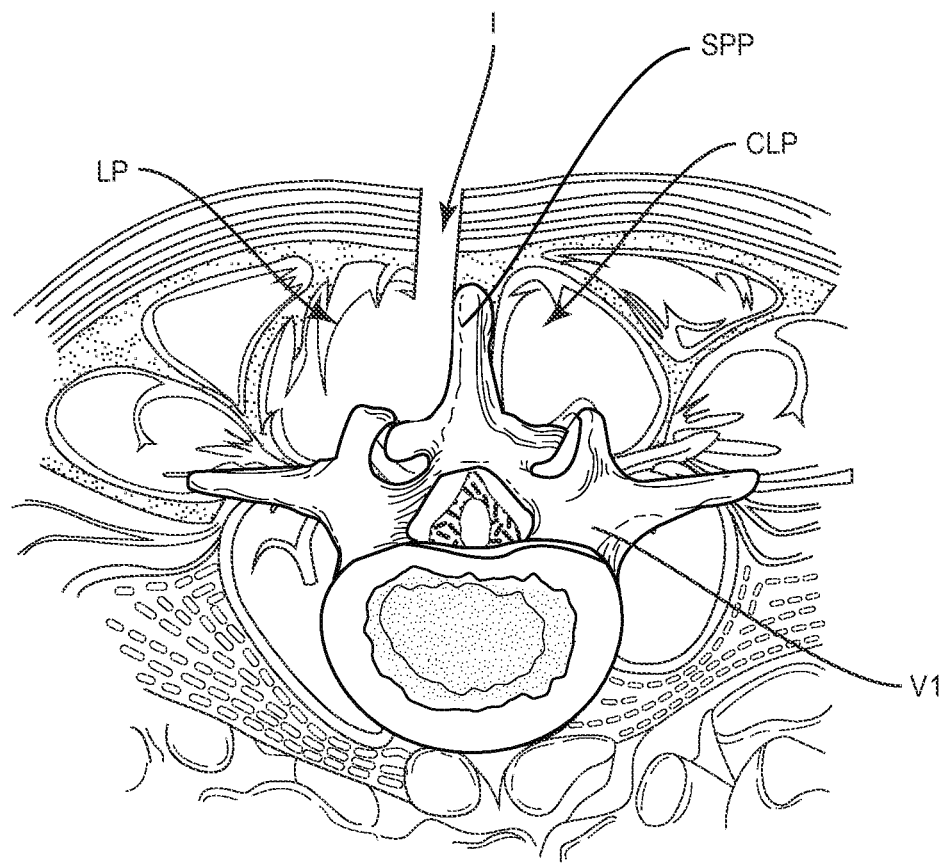
FIG. 2 is a cross section view of components of the system and the body shown in FIG. 1.

A pathway is created adjacent the surgical site along a lateral side of spinous process SPP and down the lamina to the facet of lateral portion LP. The components of spinal implant system 10 are delivered percutaneously through the pathway and/or a retractor (not shown) is disposed in the pathway created in lateral portion LP, as shown in FIG. 2, to create an access to vertebrae V of lateral portion LP. A force is applied to lateral portion LP in a direction oriented away from spinous process SPP along a plane transverse to sagittal plane SP such that at least a portion of a pars interarticularis of lateral portion LP is exposed. In some embodiments, spinal implant system 10 may be used with any existing surgical method or technique including open surgery, mini-open surgery, minimally invasive surgery including percutaneous surgical implantation, whereby vertebrae V is accessed through a micro-incision, or sleeve that provides a protected passageway to the area. Once access to the surgical site is obtained, the components of spinal implant system 10 can be delivered or implanted.

In some embodiments, pilot holes are made in vertebral levels V1, V2 of lateral portion LP through the pars interarticularis. In some embodiments, the pilot holes are approximately 2 mm to 3 mm. In some embodiments, the pilot holes are made using a drill and the drill is re-oriented such that the drill is angled in the caudal to cephalad direction along sagittal plane SP. In one embodiment, the drill is oriented such that drill is inclined at the same angle as the lamina. In some embodiments, in the axial plane, the drill is moved five degrees toward spinous process SPP. In some embodiments, the drill is advanced slowly using irrigation to prevent injury to vertebrae V.

Figure 3:
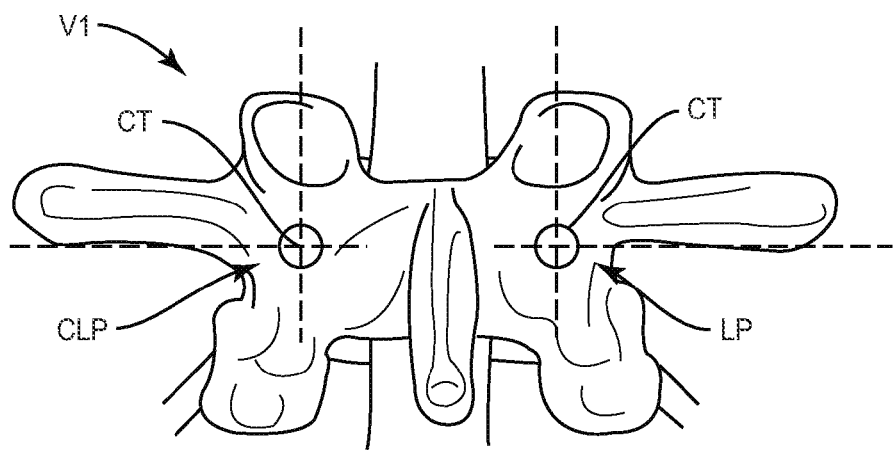
FIG. 3 is a plan view of one embodiment of trajectory for vertebrae of the body shown in FIG. 1.
Figure 4:
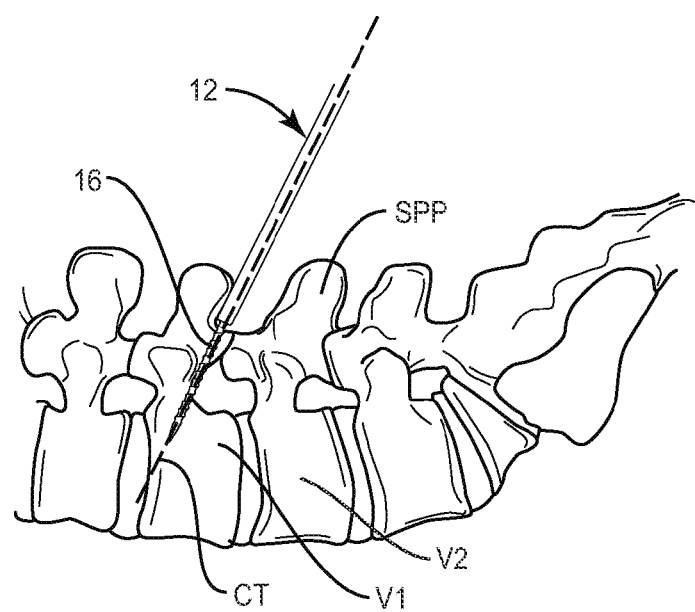
FIG. 4 is a top view of components of the system and the body shown in FIG. 1.

With lateral portion LP manipulated to expand the opening of incision I, fasteners 16, 18 and spinal rod 28 are delivered through incision I. Fastener 16 is delivered along a pathway, such as, for example, a cortical trajectory CT disposed in alignment with vertebral level V1, as shown in FIGS. 3 and 4. In one embodiment, cortical trajectory CT is determined using physical landmarks and fluoroscopy simultaneously. Fastener 18 is delivered along a cortical trajectory CT, similar to trajectory CT corresponding to fastener 16, disposed in alignment with vertebral level V2. Cortical trajectories CT are offset from sagittal plane SP. Extender 12 is employed to fasten one or more of fasteners 16, 18 and is disposed to resist engagement with spinous process SPP of vertebral levels V1, V2. In some embodiments, cortical trajectories CT are disposed in planes disposed in substantially parallel alignment with sagittal plane SP. In one embodiment, cortical trajectories CT are approximately 20 degrees medial-to-lateral and 30 degrees caudal-to-cephalad.

Figure 5:
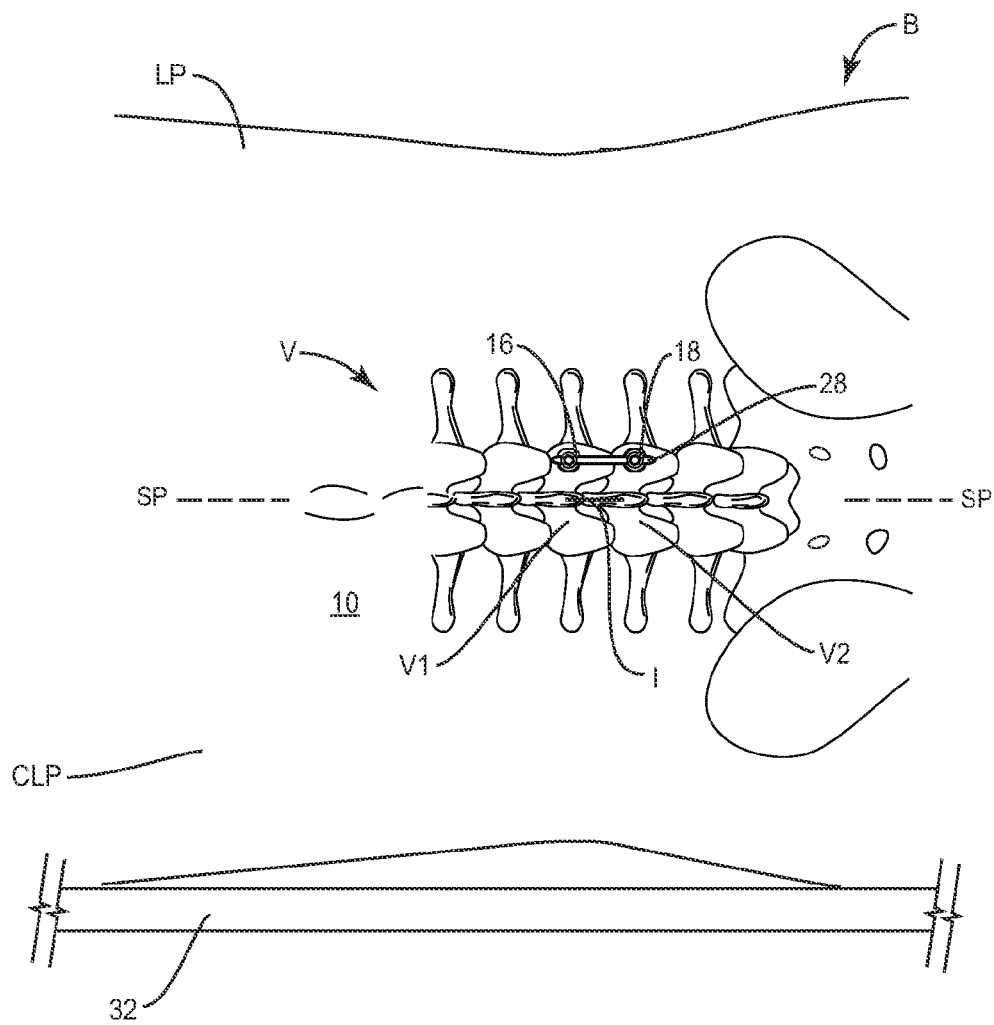
FIG. 5 is a plan view of components of the system and the body shown in FIG. 1.

Fastener 16 is fastened with vertebral level V1 adjacent lateral portion LP such that fastener 16 is approximately 3 mm to 5 mm medial to the lateral edge of a pars interarticularis. Fastener 18 is similarly fastened with vertebral level V2 adjacent lateral portion LP. Spinal rod 28 is connected with fasteners 16, 18 by inserting spinal rod 28 through the U-shaped passageways of fasteners 16, 18 and securing spinal rod 28 with set screws, as shown in FIG. 5.

The tissue includes contralateral portion CLP disposed adjacent incision I, as shown in FIG. 6. Contralateral portion CLP is manipulated to create an opening and access path to a surgical site including vertebrae V of contralateral portion CLP without selectively manipulating lateral portion LP. For example, a dorsolumbar fascia of contralateral portion CLP is opened exposing an erector spinae aponeurosis. A dissection is made along spinous process SPP over the lamina to elevate the multifidus to provide a lateral window to the lamina and articular process of contralateral portion CLP.

A pathway is created adjacent the surgical site along a contralateral side of spinous process SPP and down the lamina to the facet of contralateral portion CLP. The components of spinal implant system 10 are delivered percutaneously through the pathway and/or a retractor (not shown) is disposed in the pathway created in contralateral portion CLP, as shown in FIG. 6, to create an access to vertebrae V of contralateral portion CLP. A force is applied to contralateral portion CLP in a direction oriented away from spinous process SPP along a plane of the body transverse to the sagittal plane SP such that at least a portion of a pars interarticularis of contralateral portion CLP is exposed. Once access to the surgical site is obtained, the components of spinal implant system 10 can be delivered or implanted.

In some embodiments, pilot holes are made in vertebral levels V1, V2 of contralateral portion CLP through the pars interarticularis. With contralateral portion CLP manipulated to expand the opening of incision I, fasteners 20, 22 and spinal rod 30 are delivered through incision I. Fastener 20 is delivered along a cortical trajectory CT, as described herein, disposed in alignment with vertebral level V1. Fastener 22 is delivered along a cortical trajectory CT, as described herein, disposed in alignment with vertebral level V2. Extenders, similar to those described herein, are employed to fasten one or more of fasteners 20, 22 and are disposed to resist engagement with spinous process SPP of vertebral levels V1, V2.

Figure 7:
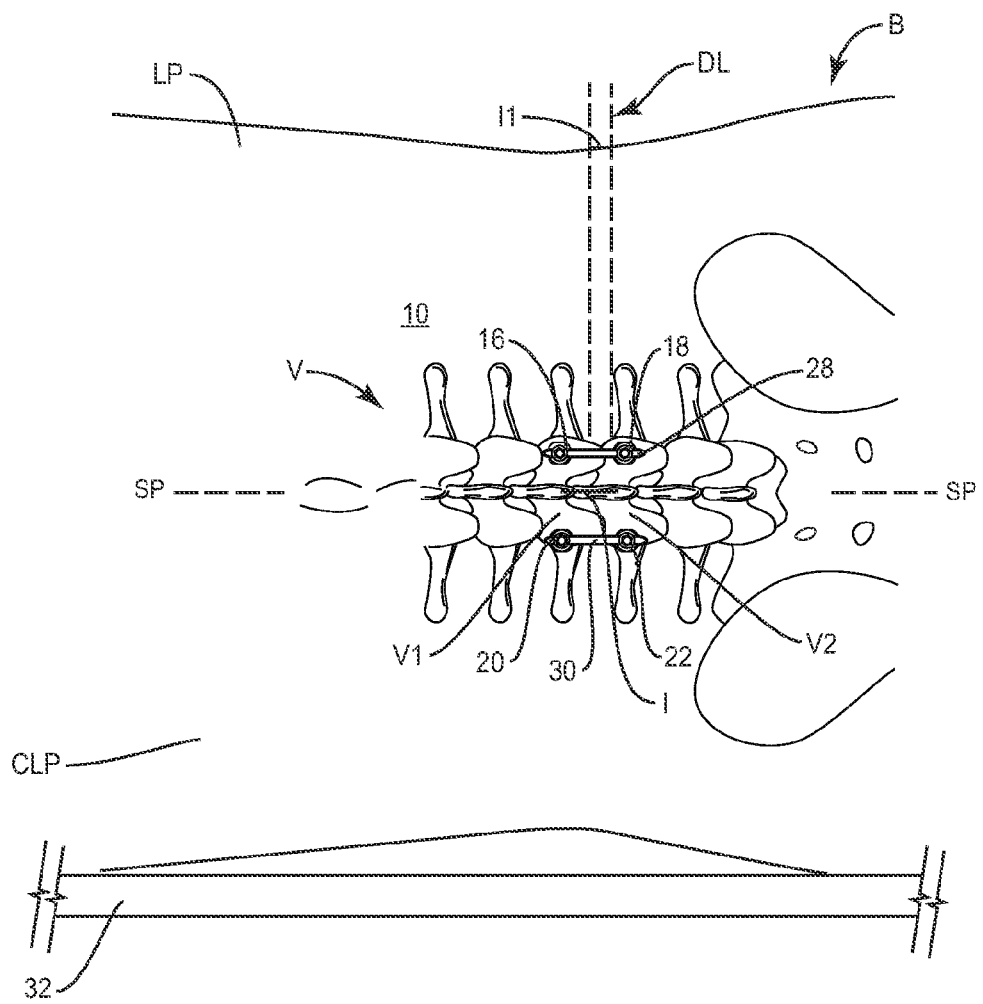
FIG. 7 is a plan view of components of the system and the body shown in FIG. 1.

Fastener 20 is fastened with vertebral level V1 adjacent contralateral portion CLP such that fastener 20 is approximately 3 mm to 5 mm medial to the lateral edge of a pars interarticularis. Fastener 22 is similarly fastened with vertebral level V2 adjacent contralateral portion CLP. Spinal rod 30 is connected with fasteners 20, 22 by inserting spinal rod 30 through the U-shaped passageways of fasteners 20, 22 and securing spinal rod 30 with set screws. Rods 28, 30 are disposed in a bilateral configuration with vertebral levels V1, V2, as shown in FIG. 7. In some embodiments, lateral portion LP and contralateral portion CLP are treated without moving body B, relative to table 32, from the lateral orientation or the prone orientation.

In one embodiment, as shown in FIG. 7, while maintaining body B in a selected orientation, such as a prone or a lateral orientation, and not rotating body B from the selected orientation relative to surgical table 32, an interbody implant (not shown) is delivered along a direct lateral surgical approach or pathway DL adjacent to a surgical site and implanted adjacent vertebral levels V1, V2. In the lateral orientation, a medical practitioner obtains access to a surgical site including vertebral level V1 and vertebral level V2 via a lateral incision I1 with body B through pathway DL, which includes a protected passageway, similar to those described herein. In one embodiment, the interbody implant is delivered along pathway DL and implanted with levels V1 and/or V2 in connection with a partial or complete corpectomy, which is performed for treating the spine disorder.

Upon completion of a procedure, described herein, the surgical instruments, assemblies and non-implanted components of spinal implant system 10 are removed and the incisions are closed. One or more of the components of spinal implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10. In some embodiments, spinal implant system 10 may include one or a plurality of plates, connectors and/or bone fasteners for use with a single vertebral level or a plurality of vertebral levels.

In one embodiment, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

In one embodiment, spinal implant system 10, similar to the systems described above, includes unilateral bone fasteners, such as, for example, facet screws (not shown) similar to the fasteners described above, and a bone plate (not shown), and is employed with a surgical procedure for treatment of a spinal disorder, similar to the methods described above. Body B (FIG. 7) is disposed in a selected orientation, as described above, relative to surgical table 32 and access to the surgical site is obtained through a single minimally invasive incision in tissue, described above, such that the facet screws can be delivered or implanted with portion CLP.

A pilot hole is made in vertebral level V1 of portion CLP via the incision through articular facets of vertebral level V1 and/or adjacent vertebrae along a facet screw trajectory. The facet screw is delivered through the incision to the surgical site along the facet screw trajectory. The facet screw is fastened via an extender to immobilize the articular facets of vertebral level V1 and/or adjacent vertebrae to support portion CLP of vertebrae V. A pilot hole is made in vertebral level V2 of portion CLP via the incision through articular facets of vertebral level V2 and/or adjacent vertebrae along a facet screw trajectory. The facet screw is delivered through the incision to the surgical site along the facet screw trajectory. The facet screw is fastened via an extender to immobilize the articular facets of vertebral level V2 and/or adjacent vertebrae to support portion CLP of vertebrae V.

While maintaining body B in the lateral orientation and not rotating body B from the lateral orientation relative to surgical table 32, a medical practitioner obtains access to a surgical site including vertebral levels V1, V2 via a lateral incision with body B that communicates with a direct lateral surgical pathway. The bone plate is delivered through the lateral incision and along the direct lateral surgical pathway adjacent to a surgical site for implantation with an anterior portion of levels V1, V2 to support portion LP of vertebrae V.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method for treating a spine, the method comprising the steps of:

creating a single minimally invasive incision in tissue of a body along a substantially sagittal plane of the body;

manipulating a lateral portion of the tissue without manipulating a contralateral portion of the tissue to deliver a first fastener, a second fastener and a first spinal rod through the incision, the first fastener being delivered along a cortical trajectory disposed in alignment with a first vertebral level and the second fastener being delivered along a cortical trajectory disposed in alignment with a second vertebral level;

fastening the first fastener with the first vertebral level adjacent the lateral portion;

fastening the second fastener with the second vertebral level adjacent the lateral portion;

connecting the first spinal rod with the fasteners;

manipulating the contralateral portion without manipulating the lateral portion to deliver a third fastener, a fourth fastener and a second spinal rod through the incision, the third fastener being delivered along a cortical trajectory disposed in alignment with the first vertebral level and the fourth fastener being delivered along a cortical trajectory disposed in alignment with the second vertebral level;

fastening the third fastener with the first vertebral level adjacent the contralateral portion;
fastening the fourth fastener with the second vertebral level adjacent the contralateral portion; and
connecting the second spinal rod with the third and fourth fasteners.

2. A method as recited in claim 1, wherein the first fastener is fastened with a pars interarticularis of the first vertebral level.

3. A method as recited in claim 1, wherein the body is disposed in a lateral orientation relative to a surgical fixed surface configured for supporting the body.

4. A method as recited in claim 3, further comprising the step of maintaining the body in the lateral orientation relative to the surgical fixed surface during the steps of manipulating and fastening the fasteners.

5. A method as recited in claim 1, wherein the body is disposed in a prone orientation relative to a surgical fixed surface configured for supporting the body.

6. A method as recited in claim 1, wherein the cortical trajectory is offset from the sagittal plane of the body.

7. A method as recited in claim 1, wherein the cortical trajectory is offset from the sagittal plane of the body and the step of fastening includes manipulating an extender to fasten one or more of the fasteners such that the extender is disposed to resist engagement with a spinous process of the first or second vertebral levels.

8. A method as recited in claim 1, wherein the first fastener and the second fastener are relatively disposed in a substantially parallel orientation.

9. A method as recited in claim 1, wherein the rods are disposed in a bilateral configuration relative to the vertebral levels.

10. A method as recited in claim 1, wherein the contralateral portion is disposed between the lateral portion and a surgical fixed surface configured for supporting the body.

11. A method as recited in claim 1, wherein the lateral portion includes a pars interarticularis of the first vertebral level and a pars interarticularis of the second vertebral level.

12. A method as recited in claim 1, wherein the contralateral portion includes a pars interarticularis of the first vertebral level and a pars interarticularis of the second vertebral level.

13. A method as recited in claim 1, further comprising the step of delivering an interbody implant along a direct lateral trajectory adjacent the first vertebral level.

14. A method as recited in claim 13, further comprising the step of maintaining the body in a lateral orientation relative to a surgical fixed surface during the step of delivering the interbody implant.

15. A method as recited in claim 13, wherein the interbody implant includes an expandable cage.

16. A method as recited in claim 1, further comprising the steps of delivering a plate along a direct lateral trajectory adjacent the first vertebral level and fastening the plate with the first vertebral level.

17. A method for treating a spine, the method comprising the steps of:
disposing a body including vertebrae in a lateral orientation relative to a surgical fixed surface configured for supporting the body;
creating a single minimally invasive incision in tissue of the body along a substantially sagittal plane of the body;
manipulating a lateral portion of the tissue without manipulating a contralateral portion of the tissue to deliver a first fastener, a second fastener and a first spinal rod through the incision, the first fastener being delivered along a cortical trajectory disposed in alignment with a first vertebral level of the vertebrae and the second fastener being delivered along a cortical trajectory disposed in alignment with a second vertebral level of the vertebrae;
fastening the first fastener with the first vertebral level adjacent the lateral portion;
fastening the second fastener with the second vertebral level adjacent the lateral portion;
connecting the first spinal rod with the fasteners;
manipulating the contralateral portion without manipulating the lateral portion to deliver a third fastener, a fourth fastener and a second spinal rod through the incision, the third fastener being delivered along a cortical trajectory disposed in alignment with the first vertebral level and the fourth fastener being delivered along a cortical trajectory disposed in alignment with the second vertebral level;
fastening the third fastener with the first vertebral level adjacent the contralateral portion;
fastening the fourth fastener with the second vertebral level adjacent the contralateral portion;
connecting the second spinal rod with the third and fourth fasteners; and
maintaining the body in the lateral orientation relative to the surgical fixed surface during the steps of manipulating and fastening the fasteners.

18. A method as recited in claim 17, further comprising the step of delivering an interbody implant along a direct lateral trajectory adjacent the first vertebral level.

19. A method as recited in claim 17, further comprising the steps of delivering a plate along a direct lateral trajectory adjacent the first vertebral level and fastening the plate with the first vertebral level.

20. A method for treating a spine, the method comprising the steps of:
disposing a body including vertebrae in a lateral orientation relative to a surgical fixed surface configured for supporting the body;
creating a single minimally invasive incision in tissue of the body along a substantially sagittal plane of the body;
manipulating a lateral portion of the tissue without manipulating a contralateral portion of the tissue to deliver a first fastener, a second fastener and a first spinal rod through the incision, the first fastener being delivered along a cortical trajectory disposed in alignment with a first vertebral level of the vertebrae and the second fastener being delivered along a cortical trajectory disposed in alignment with a second vertebral level of the vertebrae;
fastening the first fastener with the first vertebral level adjacent the lateral portion;
fastening the second fastener with the second vertebral level adjacent the lateral portion;
connecting the first spinal rod with the fasteners;
manipulating the contralateral portion without manipulating the lateral portion to deliver a third fastener, a fourth fastener and a second spinal rod through the incision, the third fastener being delivered along a cortical trajectory disposed in alignment with the first vertebral level and the fourth fastener being delivered along a cortical trajectory disposed in alignment with the second vertebral level;
fastening the third fastener with the first vertebral level adjacent the contralateral portion;
fastening the fourth fastener with the second vertebral level adjacent the contralateral portion;

connecting the second spinal rod with the third and fourth fasteners;

maintaining the body in the lateral orientation relative to the surgical fixed surface during the steps of manipulating and fastening the fasteners; and delivering an interbody implant along a direct lateral trajectory adjacent the first vertebral level without moving the body from the lateral orientation.

\* \* \* \* \*